United States Patent [19]

Gottschalk et al.

[11] Patent Number: 4,937,159
[45] Date of Patent: Jun. 26, 1990

[54] PHOTOSENSITIVE MATERIALS AND COMPOSITIONS CONTAINING IONIC DYE COMPOUNDS AS INITIATORS AND THIOLS AS AUTOOXIDIZERS

[75] Inventors: Peter Gottschalk, Centerville; Douglas C. Neckers, Perrysburg, both of Ohio; Gary B. Schuster, Champaign, Ill.; Paul C. Adair, Springboro, Ohio; S. Peter Pappas, Fargo, N. Dak.

[73] Assignee: The Mead Corporation, Dayton, Ohio

[21] Appl. No.: 281,303

[22] Filed: Dec. 7, 1988

Related U.S. Application Data

[63] Continuation of Ser. No. 180,915, Apr. 13, 1988, abandoned, which is a continuation-in-part of Ser. No. 944,305, Dec. 18, 1986, Pat. No. 4,772,530, which is a continuation-in-part of Ser. No. 860,367, May 6, 1986, abandoned, which is a continuation-in-part of Ser. No. 800,014, Nov. 20, 1985, abandoned.

[51] Int. Cl.$^5$ ............................ G03C 1/68; G03C 1/72
[52] U.S. Cl. ..................................... 430/138; 430/281; 430/339; 430/495; 430/914; 430/916; 522/25; 522/26; 522/31; 522/27
[58] Field of Search ............... 430/281, 138, 339, 495, 430/914, 916; 522/25, 26, 31, 27

[56] References Cited

U.S. PATENT DOCUMENTS

| | | | |
|---|---|---|---|
| 2,875,047 | 3/1959 | Oster | 96/35 |
| 3,099,558 | 7/1963 | Levinos | 522/25 |
| 3,418,118 | 4/1968 | Thommes et al. | 96/11 |
| 3,488,269 | 1/1970 | Allen et al. | 204/159 |
| 3,495,987 | 4/1970 | Moore | 96/115 |
| 3,531,281 | 5/1970 | Rust | 96/48 |
| 3,547,633 | 11/1970 | Rust | 96/42.5 |
| 3,558,387 | 1/1971 | Bassemir et al. | 156/99 |
| 3,567,453 | 11/1971 | Borden | 69/91 |
| 3,573,922 | 10/1971 | Rust | 96/115 |
| 3,579,339 | 9/1971 | Chang et al. | 96/74 |
| 3,615,452 | 8/1971 | Cerwonka | 96/35.1 |
| 3,650,927 | 7/1972 | Levinos | 204/159.24 |
| 3,708,296 | 1/1973 | Schlesinger | 522/25 |
| 3,729,313 | 11/1973 | Smith | 96/27 |
| 4,001,017 | 1/1977 | Baumann et al. | 430/281 |
| 4,026,705 | 7/1977 | Crivello et al. | 96/27 |
| 4,264,703 | 8/1981 | Crivello | 430/270 |
| 4,272,589 | 9/1981 | DuBois et al. | 156/99 |
| 4,307,182 | 4/1981 | Dalzell et al. | 430/339 |
| 4,318,766 | 3/1982 | Smith et al. | 522/25 |
| 4,343,891 | 10/1982 | Aasen et al. | 430/337 |
| 4,394,403 | 10/1983 | Smith | 427/42 |
| 4,399,209 | 11/1983 | Sanders et al. | 430/138 |
| 4,405,394 | 9/1983 | Cohen | 156/308.6 |
| 4,450,227 | 12/1984 | Holmes et al. | 430/339 |
| 4,587,200 | 5/1986 | Tamoto et al. | 430/281 |
| 4,588,664 | 10/1986 | Fielding et al. | 430/1 |
| 4,751,102 | 6/1988 | Adair et al. | 430/339 |
| 4,772,541 | 9/1988 | Gottschalk et al. | 430/339 |
| 4,788,124 | 11/1988 | Wright | 430/138 |
| 4,800,149 | 1/1989 | Gottschalk et al. | 430/138 |
| 4,801,392 | 1/1989 | Adair et al. | 522/25 |
| 4,816,368 | 3/1989 | Skaggs | 430/138 |

FOREIGN PATENT DOCUMENTS 567776  3/1945  United Kingdom ............ 156/275.5

OTHER PUBLICATIONS

Eaton, "Dye Sensitized Photopolymerization", *Advances in Photochem.*, vol. 13, pp. 427–487.

Kavarnos et al., "Photosensitization by Reversible Electron Transfer: Theories, Experimental Evidence, and Examples", *Chem. Rev.*, 1986, 86, 401, 449.

Chaberek et al., "Dye–Sensitized Photopolymerization Process Kinetics and Mechanism", *J. Phys. Chem.*, 1965, 69, 2842–2848.

Eaton, "Electron Transfer of Induced Photofragmentation as a Route to Free Radicals", *Pure and Applied. Chem.*, 56, No. 9, pp. 1191–1202, 1984.

Margerum et al., "Studies on the Mechanism of Dye—Sensitized Photopolymerization Initiation", pp. 634–644.

Nagabhushaman, "Dye-Sensitized Photopolymerization of Vinyl Monomers in the Presence of Ascorbic Acid", *g. of Polym. Sci.*, 10, 1511–1528, 1972.

Neumann, "The Photoreduction of Methylene Blue by Arylaminomethane-Sulfonates", *Photochem. and Photobio.*, 39, No. 1, pp. 31–36, 1984.

Foote, "Mechanism of Photosensitized Oxidation" *Science*, Nov. 29, 1968, vol. 162, No. 3857, pp. 963–970.

Davidson et al., "Photosensitized Oxidation of Amines", *j.c.s. Perkin II*, pp. 169–180.

Sugawara, "Holographic Recording by Dye–Sensitized Photopolymerization of Acryl–amide", *Applied Optics*, vol. 14, No. 2, Feb. 1975, pp. 378–382.

Ketley, "Dye–Sensitized Photopolymerization–AR Review", *J. Rad. Cur.*

Allen et al., "Effect of Viscosity on Dye–sensitized Free Radical Photopolymerization Processes", *P. S. and E.* vol. 9, pp. 148–153.

Margerum, "Photopolymerization Mechanisms", *J. Phys. Chem.*, vol. 75, No. 20, 1971, pp. 3066–3074.

Chang et al., "Color Print Systems Based on Dispersion Photopolymerization", *Photographic Sci. and Eng.*, vol. 13, No. 2, pp. 84, 89 (1969).

*J.C.S. Chem. Comm.* 1971, "Xanthane-dye Photo-sensitized Decomposition of a Diazonium Salt", by Patricia E. Macrae and Terry R. Wright.

*Primary Examiner*—Paul R. Michl
*Assistant Examiner*—Patrick A. Doody
*Attorney, Agent, or Firm*—Smith & Schnacke

[57] ABSTRACT

A photohardenable composition comprising a free radical addition polymerizable or crosslinkable compound and an ionic dye-counter ion compound, said compound being capable of absorbing actinic radiation and producing free radicals which initiate free radical polymerization or crosslinking of said compound; and photosensitive materials incorporating the same.

24 Claims, No Drawings

PHOTOSENSITIVE MATERIALS AND COMPOSITIONS CONTAINING IONIC DYE COMPOUNDS AS INITIATORS AND THIOLS AS AUTOOXIDIZERS

CROSS-REFERENCE TO RELATED APPLICATION

This application is a continuation of U.S. Application Ser. No. 180,915 filed Apr. 13, 1988, now abandoned which in turn is a continuation-in-part of U.S. Pat. Application Ser. No. 944,305, filed Dec. 18, 1986, now U.S. Pat. No. 4,772,530, which in turn is a continuation-in-part of U.S. Pat. Application Ser. No. 860,367 filed May 6, 1986, now abandoned which in turn is a continuation-in-part of U.S. Pat. Application Serial No. 800,014 filed Nov. 20, 1985 now abandoned.

BACKGROUND OF THE INVENTION

The present invention relates to novel photohardenable compositions and to photosensitive materials employing them. More particularly, it relates to free radical addition polymerizable compositions containing an ionic dye-counter ion complex such as a cationic dye-borate anion complex or an anionic dye-iodonium ion complex as a photoinitiator.

U.S. Pats. Nos. 4,399,209 and 4,440,846 to The Mead Corporation describe imaging materials and imaging processes in which images are formed through exposure controlled release of an image-forming agent from a microcapsule containing a photohardenable composition. The imaging material is exposed image-wise to actinic radiation and subjected to a uniform rupturing force. Typically the image-forming agent is a color precursor which is released image-wise from the microcapsules whereupon it reacts with a developer to form a visible image.

One of the problems which has been encountered in designing commercially acceptable panchromatic, full color imaging materials employing these techniques has been the relatively short wavelengths band to which most photohardenable compositions are sensitive to actinic radiation. In most cases, the compositions are only sensitive to ultraviolet radiation or blue light, e.g., 350 to 480 nm.

Full color photosensitive materials are described in U.S. Pat. Application Ser. No. 339,917, filed Jan. 18, 1982, and U.S. Pat. Application Ser. No. 620,994 filed Jun. 15, 1984. These imaging materials include a photosensitive layer which contains three sets of microcapsules. Each set of microcapsules is sensitive to a different band of radiation in the ultraviolet or blue spectrum and contains a cyan, magenta or yellow image-forming agent. The absorption spectra of the initiators employed in these microcapsules are never perfectly distinct. There is always some degree of overlap in the absorption curves and sometimes it is substantial. Exposure conditions therefore must be controlled carefully to avoid cross-exposure.

It would be desirable to extend the sensitivity of the photohardenable compositions used in these imaging materials to longer wavelengths. By extending the sensitivity of the photohardenable compositions to longer wavelengths, the amount of overlap in the absorption spectra of the initiators and the concomitant incidence of cross-exposure can be reduced. It would be particularly desirable if compositions could be designed with sensitivities to selected wavelength bands throughout the visible spectrum (400 to 700 nm) since this would provide a visible light-sensitive material which could be exposed by direct reflection or transmission imaging and without image processing.

SUMMARY OF THE INVENTION

It has been found that ionic dye-counter ion compounds, such as cationic dye-borate anion compounds, are useful photoinitiators of free radical addition reactions. Such compounds consist of a visible light absorber (the ionic dye) ionically bonded to a reactive counter ion. The counter ion is reactive in the sense that upon excitation of the dye the counter ion donates an electron to or accepts an electron from the excited dye. This electron transfer process generates radicals capable of initiating polymerization of a monomer.

The mechanism whereby the compounds absorb energy and generate free radicals is not entirely clear. It is believed that upon exposure to actinic radiation, the dye ion is excited to an excited singlet state in which it accepts an electron from or donates an electron to the counter ion. For a cationic dye-borate anion compound, this can be illustrated by the following equation:

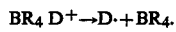

$$BR_4^- D^+ \rightarrow D\cdot + BR_4\cdot$$

The lifetime of the dye singlet state is extremely short by comparison to the lifetime of the triplet state. The quenching rate constants which have been observed suggest that the ionic compounds experience a very efficient electron transfer via the singlet state. In solution in the polymerizable compound, tight ionic pairing of the counter ion and the dye is believed to provide favorable spacial distribution promoting electron transfer to such an extent that the transfer occurs even though the lifetime of the singlet state is very short. Of course, this does not mean that electron transfer is restricted to the singlet state. Ionic dyes which have significant populations of triplet state may undergo electron transfer through the singlet state, triplet state, or both singlet and triplet states.

Upon transfer of the electron, a radical is formed. Many of the ionic compounds used as initiators in the present invention do not appear to exhibit significant back electron transfer. It is believed that following electron transfer, the dye and counter ion become disassociated such that back electron transfer does not occur.

The ionic compounds used in the present invention are different than the collision generated species encountered in other photosensitive systems such as collision complexes which yield encounter complexes, exciplexes and/or contact ion pairs. See for example, Kavarnos, George J. and Turro, Nicholas J., "Photosensitization by Reversible Electron Transfer", *Chem. Rev.* 1986, 401–449.

In accordance with the present invention the ionic dye an the counter ion are present in the photopolymerizable composition as a stable, non-transient compound, and not as a dissociated ion pair. Formation of the compound is not dependent upon diffusion and collision. As distinguished from photographic materials and compositions containing collision dependent complexes essentially all of the sensitizing dye present in the photosensitive materials of the present invention prior to exposure is ionically bonded to the counter ion.

The ionic compounds used as initiators in the present invention can also be characterized in that they are soluble in nonpolar solvents such as TMPTA and the like. They are soluble in an amount of at least about 0.1% and preferably at least about 0.3% by weight. While these amounts are not large, they are substantial considering the normally lower solubility of ionic materials in polar solvents. While the compounds are soluble, the dye and the counter ion do not dissociate in solution. They remain ionically bonded to each other.

In dye-sensitized photopolymerizable compositions, visible light is absorbed by a dye having a comparable absorption band, the dye is raised to its excited electronic state, the lifetime of which may be $10^{-9}$ to $10^{-3}$ second, depending upon the nature (singlet or triplet) of the excited state. During this time, the absorbed energy allows an electron to be transferred to or from the dye molecule to produce the free radical. In prior initiator systems, this transfer is diffusion controlled. The excited dye must interact (collide) with another molecule in the composition which quenches the dye and generates a free radical. In the present invention, the efficiency with which the excited state is utilized is not limited by diffusion.

Thus, the present invention provides a means for generating free radicals from the excited state of an ionic dye and insodoing provides photohardenable compositions which are sensitive at longer wavelengths.

One of the particular advantages of using ionic dye-counter ion compounds as initiators of free radical addition reactions is the ability to select from a wide variety of dyes which absorb at substantially different wavelengths. The absorption characteristics of the compound are principally determined by the dye. Thus, by selecting a dye which absorbs at 400 nm or greater, the sensitivity of the photosensitive material can be extended well into the visible range. Furthermore, compounds can be selected which are respectively sensitive to red, green and blue light without substantial cross-talk.

The ionic dye-counter ion compounds are particularly useful in providing full color photosensitive materials. In these materials, a layer including three sets of microcapsules having distinct sensitivity characteristics is provided on a support. Each set of microcapsules respectively contains a cyan, magenta, or yellow color-forming agent.

The absorption characteristics of the three sets of microcapsules in a full color photosensitive material must be sufficiently different that the cyan-forming capsules can be differentially hardened at a predetermined wavelength or over a predetermined wavelength range without hardening the magenta or yellow-forming capsules and, likewise, the magenta-forming and yellow-forming capsules can be selectively hardened upon exposure respectively to second and third wavelengths without hardening the cyan-forming capsules or hardening the other of the yellow-forming or magenta-forming capsules. Microcapsules having this characteristic (i.e., cyan-, magenta- and yellow-forming capsules which can be selectively hardened by exposure at distinct wavelengths without cross-exposure) are referred to herein as having "distinctly different sensitivities."

As indicated above, because most photohardenable compositions are sensitive to ultraviolet radiation or blue light and they tend not to be sensitive to wavelengths greater than about 480 nm, it has been difficult to achieve microcapsules having distinct sensitivities at three wavelengths. Often it can only be achieved by carefully adjusting the exposure amounts so as not to cross-expose the capsules.

The present invention facilitates the achievement of distinct sensitivities by shifting the peak absorption of at least one of the initiators to higher wavelengths, such as wavelengths greater than about 400 nm. In this manner, instead of attempting to establish distinct sensitivities at three wavelengths within the narrow wavelength range of, for example, 350 nm to 480 nm, sensitivity can be established over a broader range of, for example, 350 to 550 nm or higher. In accordance with the invention, the sensitivity of the microcapsules can be extended well into the visible spectrum to 600 nm and in some cases to about 700 nm. In the preferred case compounds are provided which are respectively sensitive to red, green and blue light.

In addition to use of the photoinitiators or providing full color photosensitive materials, other uses are envisioned. For example, it is contemplated that the photoinitiators may be used in connection with light curable dental adhesives, as sensitizers for photopolymer holography, in light curable coatings containing ultraviolet-absorbers for photostabilization, in three-dimensional model formation and in applying underwater coatings.

A principal object of the present invention is to provide photohardenable compositions which are sensitive to visible light, e.g., wavelengths greater than about 400 nm.

A further object of the present invention is to provide visible light-sensitive photohardenable compositions which are useful in the imaging materials described in U.S. Pats. Nos. 4,399,209 and 4,440,846.

Another object of the present invention is to provide photohardenable compositions which are sensitive at greater than about 400 nm and which are useful as photoresists or in forming polymer images.

These and other objects are accomplished in accordance with the present invention which, in one embodiment, provides:

A photohardenable composition comprising a free radical addition polymerizable or crosslinkable compound and a ionic dye-reactive counter ion compound, said ionic dye-reactive counter ion compound being capable of absorbing actinic radiation and producing free radicals which initiate free radical addition polymerization or crosslinking of said addition polymerizable or crosslinkable compound.

Another embodiment of the present invention resides in a photosensitive material comprising a support having a layer of photosensitive microcapsules on the surface thereof, said microcapsules containing an internal phase including a photohardenable composition comprising a free radical addition polymerizable or crosslinkable compound and an ionic dye-reactive counter ion compound.

Still another embodiment of the present invention resides in a photosensitive material useful in forming full color images comprising a support having a layer of photosensitive microcapsules on the surface thereof, said photosensitive microcapsules comprising a first set of microcapsules having a cyan image-forming agent associated therewith, a second set of microcapsules having a magenta image-forming agent associated therewith, and a third set of microcapsules having a yellow image-forming agent associated therewith, at least one of said first, second, and third sets of microcapsules containing an internal phase which includes a photohardenable composition including a free radical addition polymerizable or crosslinkable compound and an ionic dye-reactive counter ion compound.

A further embodiment of the present invention resides in a photosensitive material comprising a support having a layer of a photohardenable composition on the surface thereof, said photohardenable composition comprising a free radical addition polymerizable or crosslinkable compound and an ionic dye-reactive counter ion compound which provides a quenching constant (Kq) which is greater than $10^{10}$ and preferably greater than $10^{12}$.

In accordance with more particular embodiments of the invention, the ionic compound is a cationic dye-borate anion compound and still more particularly a cyanine dyeborate anion compound; or an anionic dye compound such as ionic compounds of xanthene dyes with iodonium or pyryllium ions.

DETAILED DESCRIPTION OF THE INVENTION

U.S. Pats. Nos. 4,399,209 and 4,440,846 and U.S. Pat. Applications Ser. No. 339,917, filed Jan. 18, 1982, and U.S. Pat. Ser. No. 620,994, filed Jun. 15, 1984, are incorporated herein by reference to the extent that reference thereto may be necessary to complete this disclosure.

Cationic dye-borate anion compounds are known in the art. Their preparation and use in imaging systems is described in U.S. Pats. Nos. 3,567,453; 4,307,182; 4,343,891; 4,447,521; and 4,450,227. The compounds used in the present invention can be represented by the general formula (I):

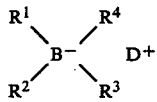
(I)

where $D^+$ is a cationic dye; and $R^1$, $R^2$, $R^3$, and $R^4$ are independently selected from the group consisting of alkyl, aryl, alkaryl, allyl, aralkyl, alkenyl, alkynyl, alicyclic and saturated or unsaturated heterocyclic groups.

Useful dyes form photoreducible but dark stable complexes with borate anions and can be cationic methine, polymethine, triarylmethane, indoline, thiazine, xanthene, oxazine and acridine dyes. More specifically, the dyes may be cationic cyanine, carbocyanine, hemicyanine, rhodamine and azomethine dyes. In addition to being cationic, the dyes should not contain groups which would neutralize or desensitize the complex or render the complex poorly dark stable. Examples of groups which generally should not be present in the dye are acid groups such as free carboxylic or sulphonic acid groups.

Specific examples of useful cationic dyes are Methylene Blue, Safranine 0, Malachite Green, cyanine dyes of the general formula (II) and rhodamine dyes of the formula (III):

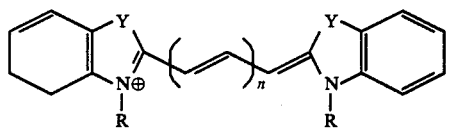
(II)

n=0, 1, 2, 3
R=alkyl

Y=CH=CH, N—CH₃, C(CH₃)₂, O, S, Se

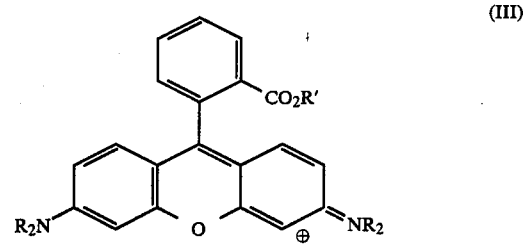
(III)

R′, R=alkyl, aryl, and any combination thereof

While they have not been tested, the cationic cyanine dyes disclosed in U.S. Pat. No. 3,495,987 should be useful in the present invention.

The borate anion is designed such that the borate radical generated upon exposure to light and after electron transfer to the dye (Eq. 1) readily dissociates with the formation of a radical as follows:

$$BR_4 \rightarrow BR_3 + R \cdot \qquad \text{(Eq. 2)}$$

For example particularly preferred anions are triphenylbutylborate and trianisylbutylborate anions because they readily dissociate to triphenylborane or trianisylborane and a butyl radical. On the other hand tetrabutylborate anion does not work well presumably because the tetrabutylborate radical is not stable and it readily accepts an electron back from the dye in a back electron transfer and does not dissociate efficiently. Likewise, tetraphenylborate anion is very poor because the phenyl radical is not easily formed.

Preferably, at least one but not more than three of $R^1$, $R^2$, $R^3$, and $R^4$ is an alkyl group. Each of $R^1$, $R^2$, $R^3$, and $R^4$ can contain up to 20 carbon atoms, and they typically contain 1 to 7 carbon atoms. More preferably $R^1$-$R^4$ are a combination of alkyl group(s) and aryl group(s) or aralkyl group(s) and still more preferably a combination of three aryl groups and one alkyl group.

Representative examples of alkyl groups represented by $R^1$-$R^4$ are methyl, ethyl, propyl, butyl, pentyl, hexyl, octyl, stearyl, etc. The alkyl groups may be substituted, for example, by one or more halogen, cyano, acyloxy, acyl, alkoxy or hydroxy groups.

Representative examples of aryl groups represented by $R^1$-$R^4$ include phenyl, naphthyl and substituted aryl groups such as anisyl. Alkaryl groups include methylphenyl, dimethylphenyl, etc. Representative examples of aralkyl groups represented by $R^1$-$R^4$ groups include benzyl. Representative alicyclic groups include cyclobutyl, cyclopentyl, and cyclohexyl groups. Examples of an alkynyl group are propynyl and ethynyl, and examples of alkenyl groups include a vinyl group.

As a general rule, useful ionic dye compounds must be identified empirically, however, potentially useful dye and counter ion combinations can be identified by reference to the Weller equation (Rehm, D. and Weller, A., *Isr. J Chem.* (1970), 8, 259–271), which can be simplified as follows.

$$\Delta G = E_{ox} - E_{red} - E_h\nu \qquad \text{(Eq. 3)}$$

where $\Delta G$ is the change in the Gibbs free energy, $E_{ox}$ is the oxidation potential of the borate anion $BR^-_4$, $E_{red}$ is the reduction potential of the cationic dye, and $E_{h\nu}$ is the energy of light used to excite the dye. Useful compounds will have a negative free energy change. Similarly, the difference between the reduction potential of the dye and the oxidation potential of the borate must be positive for the compounds to be dark stable, i.e., Eox - Ered>0.

As indicated, Eq. 2 is a simplification and it does not absolutely predict whether a compound will be useful in the present invention or not. There are a number of other factors which will influence this determination. One such factor is the effect of the monomer on the compound. Another factor is the radial distance between the ions. It is also known that if the Weller equation produces too negative a value, deviations from the equation are possible. Furthermore, the Weller equation only predicts electron transfer, it does not predict whether a particular compound is an efficient initiator of polymerization. The equation is a useful first approximation.

Specific examples of cationic dye-borate anion compounds useful in the present invention are shown in the following table with their λ max.

TABLE

| Compound No. | Structure | λmax (TMPTA) |
|---|---|---|
| 1. | [benzothiazole dye with CH₃ bridge, N-CH₂CH₃ groups; Ph₃B⊖n-C₄H₉] | 552 nm |
| 2. | [benzothiazole dye, N-C₇H₁₅ groups; Ph₃B⊖n-C₄H₉] | 568 nm |
| 3. | [benzoxazole dye, N-C₆H₁₃ groups; Ph₃B⊖n-C₆H₁₃] | 492 nm |
| 4. | [benzothiazole dye, N-CH₃ groups; Ph₃B⊖n-C₄H₉] | 428 nm |
| 5. | [phenothiazine dye with N(CH₃)₂ groups; Ph₃B⊖n-C₄H₉] | 658 nm |
| 6. | [phenazine-type dye with CH₃, NH₂ groups and N-phenyl; Ph₃B⊖n-C₄H₉] | 528 nm |

TABLE-continued

| Compound No. | Structure | λmax (TMPTA) |
|---|---|---|
| 7. | 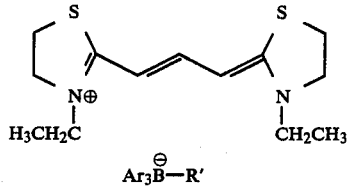 | 450 nm |

| No. | R' | Ar |
|---|---|---|
| 7A | n-butyl | phenyl |
| 7B | n-hexyl | phenyl |
| 7C | n-butyl | anisyl |

| 8. | 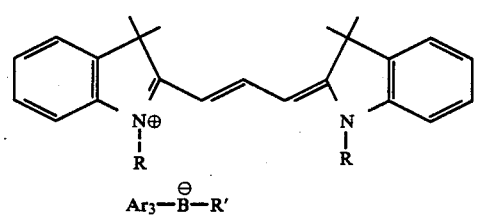 | 550 nm |
|---|---|---|

| No. | R' | R | Ar |
|---|---|---|---|
| 8A | methyl | n-butyl | phenyl |
| 8B | methyl | n-hexyl | phenyl |
| 8C | n-butyl | n-buytl | phenyl |
| 8D | n-butyl | n-hexyl | phenyl |
| 8E | n-heptyl | n-butyl | phenyl |
| 8F | n-heptyl | n-hexyl | phenyl |
| 8G | ethyl | n-butyl | phenyl |

| 9. | 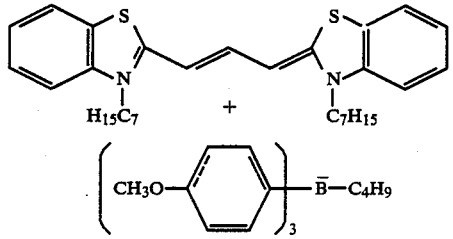 | 570 nm System |
|---|---|---|
| 10. | 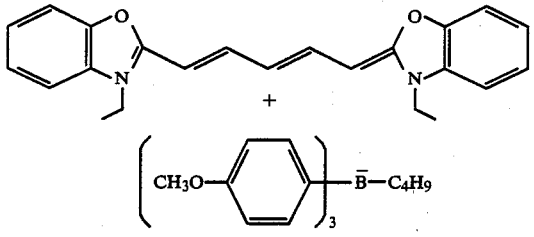 | 590 nm System |
| 11. | 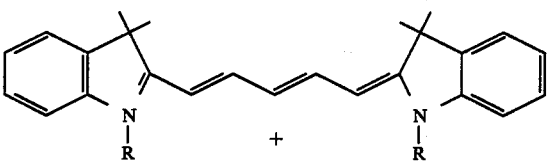 | 640 nm |

| No. | R | R' | Ar |
|---|---|---|---|
| 11A | methyl | n-butyl | phenyl |
| 11B | methyl | n-hexyl | phenyl |
| 11C | n-butyl | n-butyl | phenyl |
| 11D | n-butyl | n-hexyl | phenyl |
| 11E | n-pentyl | n-butyl | phenyl |
| 11F | n-pentyl | n-hexyl | phenyl |
| 11G | n-heptyl | n-butyl | phenyl |

TABLE-continued

| Compound No. | Structure | | | λmax (TMPTA) |
|---|---|---|---|---|
| 11H | n-heptyl | n-hexyl | phenyl | |
| 11I | methyl | n-butyl | anisyl | |
| 12. | 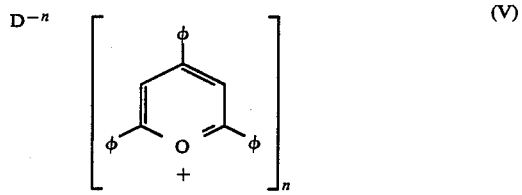 | | | 740 nm System |
| 13. | 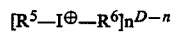 <br> 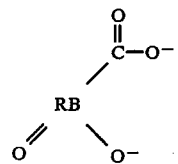 <br> Ar₃B⁻—R | | | 462 nm |
| | AR <br> phenyl | | R <br> n-butyl | |

The cationic dye-borate anion compounds can be prepared by reacting a borate salt with a dye in a counterion exchange in a known manner. See Hishiki, Y., *Repts. Sci. Research Inst.* (1953), 29, pp 72–79. Useful borate salts are sodium salts such as sodium tetraphenylborate, sodium triphenylbutylborate, sodium trianisylbutylborate and ammonium salts such as tetraethylammonium tetraphenylborate.

Anionic dye compounds are also useful in the present invention. Anionic dye-iodonium ion compounds of the formula (IV):

$$[R^5-I^\oplus-R^6]_n D^{-n} \qquad (IV)$$

where $D^-$ is an anionic dye and $R^5$ and $R^6$ are independently selected from the group consisting of aromatic nuclei such as phenyl or naphthyl and n is 1 or 2; and anionic dye-pyryllium compounds of the formula (V):

$$D^{-n} \left[ \begin{array}{c} \phi \\ \phi \quad O \quad \phi \\ + \end{array} \right]_n \qquad (V)$$

where $D^-$ and n are as defined above are typical examples of anionic dye complexes.

Representative examples of anionic dyes include xanthene and oxonol dyes. For example Rose Bengal, eosin, erythiosin, and fluorscein dyes are useful. In addition to iodonium and pyryllium ions, other compounds of anionic dyes and sulfonium and phosphonium cations are potentially useful.

As in the case of the cationic dye compounds, useful dye-cation combinations can be identified through the Weller equation as having a negative free energy.

Selected examples of anionic dye compounds are shown in Table 2 (λ max. ca. 570 nm in TMPTA). In Table 2 the symbol φ is used for a phenyl group and the structure

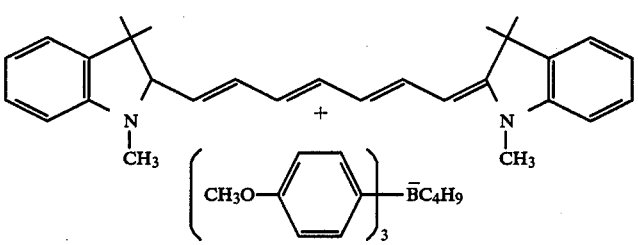

is used for

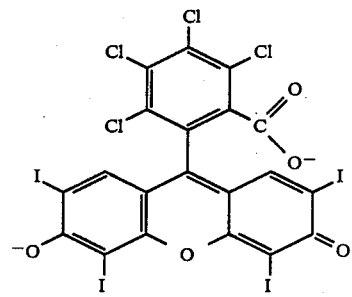

TABLE 2

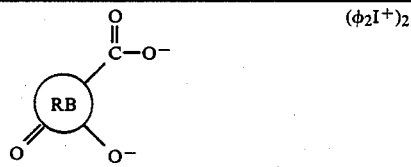

TABLE 2-continued

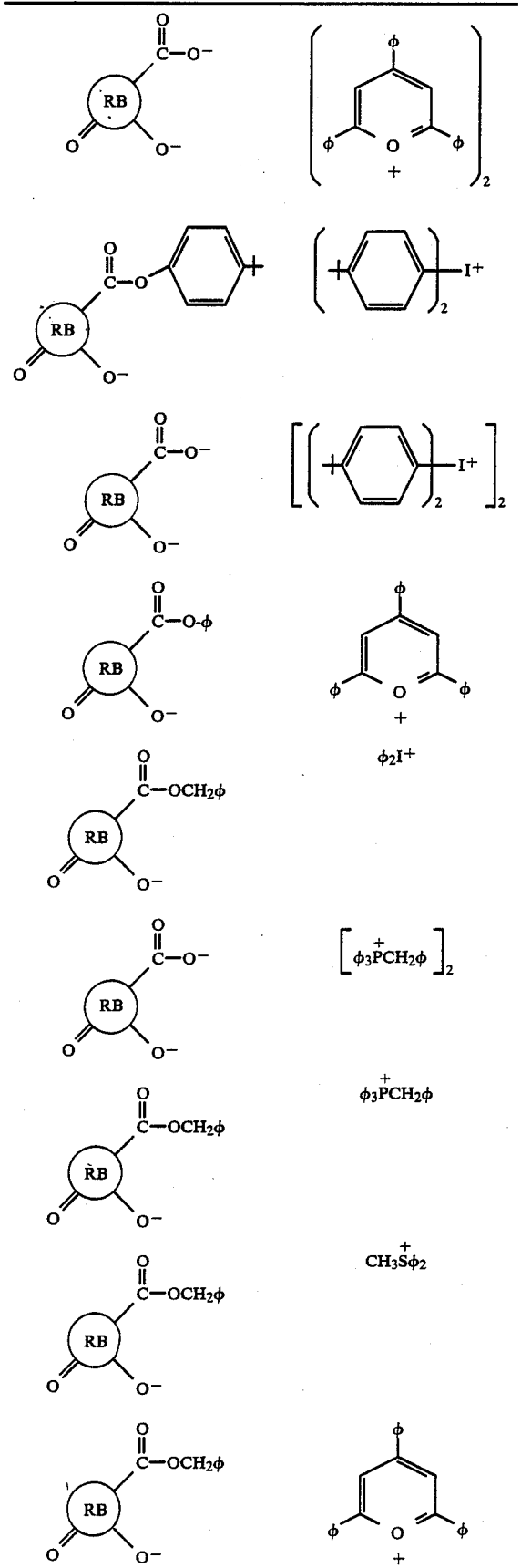
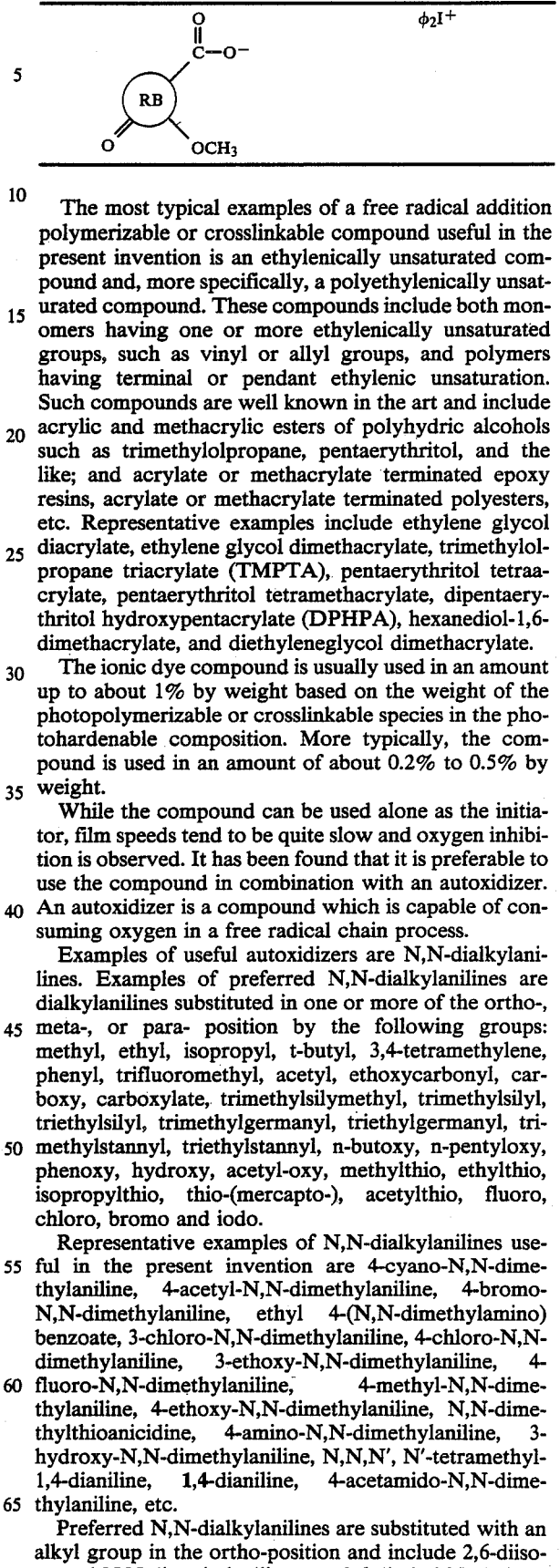

The most typical examples of a free radical addition polymerizable or crosslinkable compound useful in the present invention is an ethylenically unsaturated compound and, more specifically, a polyethylenically unsaturated compound. These compounds include both monomers having one or more ethylenically unsaturated groups, such as vinyl or allyl groups, and polymers having terminal or pendant ethylenic unsaturation. Such compounds are well known in the art and include acrylic and methacrylic esters of polyhydric alcohols such as trimethylolpropane, pentaerythritol, and the like; and acrylate or methacrylate terminated epoxy resins, acrylate or methacrylate terminated polyesters, etc. Representative examples include ethylene glycol diacrylate, ethylene glycol dimethacrylate, trimethylolpropane triacrylate (TMPTA), pentaerythritol tetraacrylate, pentaerythritol tetramethacrylate, dipentaerythritol hydroxypentacrylate (DPHPA), hexanediol-1,6-dimethacrylate, and diethyleneglycol dimethacrylate.

The ionic dye compound is usually used in an amount up to about 1% by weight based on the weight of the photopolymerizable or crosslinkable species in the photohardenable composition. More typically, the compound is used in an amount of about 0.2% to 0.5% by weight.

While the compound can be used alone as the initiator, film speeds tend to be quite slow and oxygen inhibition is observed. It has been found that it is preferable to use the compound in combination with an autoxidizer. An autoxidizer is a compound which is capable of consuming oxygen in a free radical chain process.

Examples of useful autoxidizers are N,N-dialkylanilines. Examples of preferred N,N-dialkylanilines are dialkylanilines substituted in one or more of the ortho-, meta-, or para- position by the following groups: methyl, ethyl, isopropyl, t-butyl, 3,4-tetramethylene, phenyl, trifluoromethyl, acetyl, ethoxycarbonyl, carboxy, carboxylate, trimethylsilymethyl, trimethylsilyl, triethylsilyl, trimethylgermanyl, triethylgermanyl, trimethylstannyl, triethylstannyl, n-butoxy, n-pentyloxy, phenoxy, hydroxy, acetyl-oxy, methylthio, ethylthio, isopropylthio, thio-(mercapto-), acetylthio, fluoro, chloro, bromo and iodo.

Representative examples of N,N-dialkylanilines useful in the present invention are 4-cyano-N,N-dimethylaniline, 4-acetyl-N,N-dimethylaniline, 4-bromo-N,N-dimethylaniline, ethyl 4-(N,N-dimethylamino)benzoate, 3-chloro-N,N-dimethylaniline, 4-chloro-N,N-dimethylaniline, 3-ethoxy-N,N-dimethylaniline, 4-fluoro-N,N-dimethylaniline, 4-methyl-N,N-dimethylaniline, 4-ethoxy-N,N-dimethylaniline, N,N-dimethylthioanicidine, 4-amino-N,N-dimethylaniline, 3-hydroxy-N,N-dimethylaniline, N,N,N', N'-tetramethyl-1,4-dianiline, 1,4-dianiline, 4-acetamido-N,N-dimethylaniline, etc.

Preferred N,N-dialkylanilines are substituted with an alkyl group in the ortho-position and include 2,6-diisopropyl-N,N-dimethylaniline, 2,6-diethyl-N,N-dimethylaniline, N,N,2,4,6-pentamethylaniline (PMA) and p-t-butyl-N,N-dimethylaniline.

Another useful class of autooxidizer is thiols such as mercaptobenzoxazoles, mercaptotetrazines, and mercaptotriazines. Specific examples of useful thiols include: 2-mercaptobenzothiazole, 6-ethoxy-2-mercaptobenzothiazole, 2-mercaptobenzoxazole, 4-methyl-4H-1,2,4-triazole-3-thiol, 2-mercapto-1-methylimidazole, 2-mercapto-5-methylthio-1,3,4-thiadiazole, 5-n-butylthio-2-mercapto-1,3,4-thiadiazole, 4-methoxybenzenethiol, 1-phenyl-1H-tetrazole-5-thiol, 4-phenyl-4H-1,2,4-triazole-3-thiol, 2-mercaptobenzimidazole, pentaerythritol tetrakis(mercaptoacetate), pentaerythritol tetrakis(3-mercaptoproprionate), trimethylolpropane tris (mercapto-acetate), trimethylolpropane tris(3-mercaptopropionate), 4-acetamidothiophenol, mercaptosuccinic acid, dodecanethiol, 2-mercaptopyridine, 4-mercaptopyridine, 2-mercapto-3H-quinazoline, and 2-mercaptothiazoline.

The autoxidizers are preferably used in the present invention in concentrations of about 4-5% by weight.

In some cases, the ionic dye compounds generate radicals upon heating, i.e., they behave as thermal initiators. This can cause the photosensitive composition to harden during storage at elevated temperatures which, in turn, detracts from the shelf life of the imaging system. To prevent thermal initiation and improve shelf life, it is desirable to include a thermal polymerization inhibitor in the internal phase. Where the dye is oxidized in the course of initiation, the thermal polymerization inhibitor is an antioxidant such as 2,6-di-tert-butyl-4-methylphenol. Other useful thermal polymerization inhibitors are known and can also be used to improve shelf life.

The photohardenable compositions of the present invention can be coated upon a support in a conventional manner and used as a photoresist or in photolithography to form a polymer image; or they can be encapsulated as described in U.S. Pat. Nos. 4,399,209 and 4,440,846 and used to control the release of an image-forming agent. The latter processes typically involve image-wise exposing the photosensitive material to actinic radiation and subjecting the layer of microcapsules to a uniform rupturing force such as pressure, abrasion, or ultrasonic energy whereupon the image-forming agent is released from the microcapsules for reaction with a developer.

Several processes can be used to form color images as explained in U.S. Pat. Application Ser. No. 339,917. If the microcapsules contain photosensitive compositions which are sensitive to red, green and blue light, images can be formed by direct transmission or reflection imaging or by image processing. Image processing may involve forming color separations (color-seps) corresponding to the red, green and blue component images and sequentially exposing the photosensitive material to three distinct bands of radiation hereinafter designated $\lambda$-1, $\lambda$-2, and $\lambda$-3 through each color separation. Otherwise, it may involve electronic processing in which the image or subject to be recorded is viewed through a Dunn or matrix camera and the output from the camera electronically drives three exposure sources corresponding to $\lambda$-1, $\lambda$-2, and $\lambda$-3. Alternatively, the image may be produced synthetically, e.g., a computer-generated image.

While the discussion herein relates to forming 3-color full color images, 4-color images are also possible. For example, microcapsules containing cyan, magenta, yellow, and black image-forming agents can be provided which have distinct sensitivities at four wavelengths, e.g., $\lambda$-1, $\lambda$-2, $\lambda$-3, and $\lambda$-4.

In accordance with the invention, at least one set of the microcapsules in a full color system contains an ionic dye compound. The other sets also may contain an ionic dye compound, or they may contain a different type of photoinitiator.

In accordance with the preferred embodiments of the invention, a full color imaging system is provided in which the microcapsules are sensitive to red, green, and blue light respectively. The photosensitive composition in at least one and possibly all three microcapsules are sensitized by an ionic dye compound. For optimum color balance, the microcapsules are sensitive ($\lambda$max) at about 450 nm, 550 nm, and 650 nm, respectively. Such a system is useful with visible light sources in direct transmission or reflection imaging. Such a material is useful in making contact prints or projected prints of color photographic slides. They are also useful in electronic imaging using lasers or pencil light sources of appropriate wavelengths.

Because the ionic dye compounds absorb at wavelengths greater than 400 nm, they are colored. Typically, the unexposed dye compound is present with the image-forming agent in the image areas and, thus, the color of the compound must be considered in determining the color of the image. However, the compound is used in very small amounts compared to the image-forming agent and exposure sometimes bleaches the compound.

The photohardenable compositions of the present invention can be encapsulated in various wall formers using techniques known in the area of carbonless paper including coacervation, interfacial polymerization, polymerization of one or more monomers in an oil, as well as various melting, dispersing, and cooling methods. To achieve maximum sensitivities, it is important that an encapsulation technique be used which provides high quality capsules which are responsive to changes in the internal phase viscosity in terms of their ability to rupture. Because the borate tends to be acid sensitive, encapsulation procedures conducted at higher pH (e.g., greater than about 6) are preferred.

Oil soluble materials have been encapsulated in hydrophilic wall-forming materials such as gelatin-type materials (see U.S. Pat. Nos. 2,730,456 and 2,800,457 to Green et al) including gum arabic, polyvinyl alcohol, carboxy-methylcellulose; resorcinol-formaldehyde wall formers (see U.S. Pat. No. 3,755,190 to Hart, et al); isocyanate wall-formers (see U.S. Pat. No. 3,914,511 to Vassiliades); isocyanate-polyol wall-formers (see U.S. Pat. No. 3,796,669 to Kiritani et al); urea-formaldehyde wall-formers, particularly urea-resorcinol-formaldehyde in which oleophilicity is enhanced by the addition of resorcinol (see U.S. Pat. Nos. 4,001,140; 4,087,376 and 4,089,802 to Foris et al); melamine-formaldehyde resin and hydroxypropyl cellulose (see commonly assigned U.S. Pat. No. 4,025,455 to Shackle); and UF capsules formed using pectin as a system modifier as discussed in U.S. Pat. No. 4,608,330 to Marabella.

Urea-resorcinol-formaldehyde and melamine-formaldehyde capsules with low oxygen permeability are preferred. In some cases to reduce oxygen permeability it is desirable to form a double walled capsule by conducting encapsulation in two stages.

A capsule size should be selected which minimizes light attenuation. The mean diameter of the capsules used in this invention typically ranges from approximately 1 to 25 microns. As a general rule, image resolution improves as the capsule size decreases. If the capsules become too small, they may become inaccessible in the pores or the fiber of the substrate. These very small capsules may therefore be screened from exposure by the substrate. They may also fail to rupture when exposed to pressure or other rupturing means. In view of these problems, it has been determined that a preferred mean capsule diameter range is from approximately 10 microns. Technically, however, the capsules can range in size up to the point where they become visible to the human eye.

An open phase system may also be used in accordance with the invention instead of an encapsulated one. This can be done by dispersing what would otherwise be the capsule contents throughout the coating on the substrate as discrete droplets. Suitable coatings for this embodiment include polymer binders whose viscosity has been adjusted to match the dispersion required in the coating. Suitable binders are gelatin, polyvinyl alcohol, polyacrylamide, and acrylic lattices. Whenever reference is made to "capsules" and "encapsulation" without reference to a discrete capsule wall in this specification or the appended claims, those terms are intended to include the alternative of an open phase system.

The photosensitive material of the present invention can be used to control the interaction of various image-forming agents.

In one embodiment of the present invention the capsules may contain a benign visible dye in the internal phase in which case images are formed by contacting the exposed imaging material under pressure with a plain paper or a paper treated to enhance its affinity for the visible dye. A benign dye is a colored dye which does not interfere with the imaging photochemistry, for example, by relaxing the excited state of the initiator or detrimentally absorbing or attenuating the exposure radiation.

In a preferred embodiment of the invention, images are formed through the reaction of a pair of chromogenic materials such as a color precursor and a color developer, either of which may be encapsulated with the photohardenable composition and function as the image forming agent. In general, these materials include colorless electron donating type compounds and are well known in the art. Representative examples of such color formers include substantially colorless compounds having in their partial skeleton a lactone, a lactam, a sultone, a spiropyran, an ester or an amido structure such as triarylmethane compounds, bisphenylmethane compounds, xanthene compounds, fluorans, thiazine compounds, spiropyran compounds and the like. Crystal Violet Lactone and Copiken X, IV and XI are often used. The color formers can be used alone or in combination.

The developer materials conventionally employed in carbonless paper technology are also useful in the present invention. Illustrative examples are clay minerals such as acid clay, active clay, attapulgite, etc.; organic acids such as tannic acid, gallic acid, propyl gallate, etc.; acid polymers such as phenol-formaldehyde resins, phenol acetylene condensation resins, condensates between an organic carboxylic acid having at least one hydroxy group and formaldehyde, etc.; metal salts or aromatic carboxylic acids such as zinc salicylate, tin salicylate, zinc 2-hydroxy naphthoate, zinc 3,5 di-tert butyl salicylate, zinc 3,5-di-($\alpha$-methylbenzyl)salicylate, oil soluble metal salts or phenol-formaldehyde novolak resins (e.g., see U.S. Pat. Nos. 3,672,935; 3,732,120 and 3,737,410) such as zinc modified oil soluble phenol-formaldehyde resin as disclosed in U.S. Pat. No. 3,732,120, zinc carbonate etc. and mixtures thereof.

As indicated in U.S. Pat. No. 4,399,209 and 4,440,846, the developer may be present on the photosensitive sheet (providing a so-called self-contained system) or on a separate developer sheet.

In self-contained systems, the developer may be provided in a single layer underlying the microcapsules as disclosed in U.S. Pat. No. 4,440,846. Alternatively, the color former and the color developer may be individually encapsulated in photosensitive capsules and upon exposure both capsule sets image-wise rupture releasing color former and developer which mix to form the image. Alternatively, the developer can be encapsulated in non-photosensitive capsules such that upon processing all developer capsules rupture and release developer but the color former containing capsules rupture in only the unexposed or underexposed area which are the only areas where the color former and developer mix. Still another alternative is to encapsulate the developer in photosensitive capsules and the color former in non-photosensitive capsules.

The present invention is not necessarily limited to embodiments where the image-forming agent is present in the internal phase. Rather, this agent may be present in the capsule wall of a discrete capsule or in the binder of an open phase system or in a binder or coating used in combination with discrete capsules or an open phase system designed such that the image-wise ruptured capsules release a solvent for the image-forming agent. Embodiments are also envisioned in which a dye or chromogenic material is fixed in a capsule wall or binder and is released by interaction with the internal phase upon rupturing the capsules.

The most common substrate for this invention is a transparent film since it assists in obtaining uniform development characteristics, however, paper may also be used. The paper may be a commercial impact raw stock, or special grade paper such as cast-coated paper or chrome-rolled paper. Transparent films such as polyethylene terephthalate can be used. Translucent substrates can also be used in this invention.

Synthesis Examples 1 and 2 respectively illustrate the preparation of borates and dye-borate compounds.

SYNTHESIS EXAMPLE 1

Dissolve triphenylborane in 150 ml dry benzene (1M) under nitrogen atmosphere. Place flask in a cool water bath and, while stirring, add n-BuLi, (1.1 e.g.) via syringe. A white precipitate soon formed after addition was started. Stirring is continued about 45-60 min. Dilute with 100 ml hexane and filter, washing with hexane. This resultant Li salt is slightly air unstable. Dissolve the white powder in about 200 ml distilled water and, with vigorous stirring, add aqueous solution of tetramethyl ammonium chloride (1.2 e.g. of theoretical in 200 ml). A thick white precipitate forms. Stir this aqueous mixture about 30 min. at room temperature, then filter. Wash collected white solid with distilled water.

As an alternative synthesis, to a 1.0M solution of 2.0 equivalents of 1-butene in dry, oxygen-free dichloromethane, under inert atmosphere, was added slowly dropwise with stirring, 1.0 equivalents of a 1.0M solution of dibromethane-methylsulfide complex in dichloromethane. The reaction mixture stirred at reflux for 36 hours and the dichloromethane and excess 1-butene were removed by simple distillation. Vacuum distillation of the residue afforded 0.95 equivalents of a colorless mobile oil (Bp 66-7 0.35 mm Hg, $^{11}$BNMR;bs (4.83PPM)). Under inert atmosphere, this oil was dissolved in dry, oxygen-free tetrahydrofuran to give a 1.0M solution and 3.0 equivalents of a 2.0M solution of phenylmagnesium chloride in tetrahydrofuran were added dropwise with stirring. After stirring 16 hours, the resultant solution was added slowly with vigorous stirring to 2 equivalents of tetramethylammonium chloride, as a 0.2M solution, in water. The resulting white flocculate solid was filtered and derived to afford a near quantitative amount of the desired product Mp 250-2° C., $^{11}$BNMR;bs (−3.70PPM).

SYNTHESIS EXAMPLE 2

Sonicate a suspension of a borate salt (1 g/10 ml) in MeOH, to make a very fine suspension. Protect flask from light by wrapping with aluminum foil then add 1 equivalent of dye. Stir this solution with low heat on a hot plate for about 30 min. Let cool to room temperature then dilute with 5-10 volumes of ice water. Filter the resultant solid and wash with water until washings are colorless. Suction filter to dryness. Completely dry initiator compound by low heat (about 50° C.) in a vacuum drying oven. Initiator is usually formed quantitatively. Analysis by H-NMR indicates 1:1 compound formation typically greater than 90%.

SYNTHESIS EXAMPLE 3

30 millimoles of neutral acriflavine was dissolved in 200 mls of hot $CH_3OH$. To this solution was added 30 millimoles of solid tetramethylammonium n-butyltriphenyl borate stirred in 100 mls of $CH_3OH$. To this resulting mixture was added 50 mls of acetone. The reaction solution was heated overnight and was filtered. The filtrate was treated with 500 mls of ice-water to produce 3.10 grams of acriflavine n-butyltriphenyl borate. This compound was dissolved in TMPTA at room temperature to give a yellow solution having a concentration of $7.05 \times 10^{-6}$M. A drop of this solution was placed between two microscope slides and the slides were exposed to visible light. The microscope slides locked up demonstrating that the TMPTA had polymerized.

The present invention is illustrated in more detail by the following non-limiting Examples.

EXAMPLE 1

Capsule Preparation

1. Into a 600 ml stainless steel beaker, 104 g water and 24.8 g isobutylene maleic anhydride copolymer (18%) are weighed.
2. The beaker is clamped in place on a hot plate under an overhead mixer. A six-bladed, 45° pitch, turbine impeller is used on the mixer.
3. After thoroughly mixing, 3.1 pectin (polygalacturonic acid methyl ester) is slowly sifted into the beaker. This mixture is stirred for 20 minutes.
4. The pH is adjusted to 4.0 using a 20% solution of $H_2SO_4$, and 0.1 g Quadrol (2-hydroxypropyl ethylenediamine with propylene oxide from BASF) is added.
5. The mixer is turned up to 3000 rpm and the internal phase is added over a period of 10-15 seconds. Emulsification is continued for 10 minutes.
6. At the start of emulsification, the hot plate is turned up so heating continues during emulsification.
7. After 10 minutes, the mixing speed is reduced to 2000 rpm and 14.1 g urea solution (50% w/w), 3.2 g resorcinol in 5 g water, 21.4 g formaldehyde (37%), and 0.6 g ammonium sulfate in 10 ml water are added at two-minute intervals.
8. The beaker is covered with foil and a heat gun is used to help bring the temperature of the preparation to 65° C. When 65° C. is reached, the hot plate is adjusted to maintain this temperature for a two to three hour cure time during which the capsule walls are formed.
9. After curing, the heat is turned off and the pH is adjusted to 9.0 using a 20% NaOH solution.
10. Dry sodium bisulfite (2.8 g) is added and the capsule preparation is cooled to room temperature.

Three batches of microcapsules were prepared for use in a full color imaging sheet using the three internal phase compositions set forth below. Internal Phase A provides a yellow image-forming agent and is sensitive at 420 nm, Phase B provides a magenta image-forging agent and is sensitive at 480 nm, and Phase C contains a cyan image-forming agent and cationic dye-borate anion complex which is sensitive at 570 nm. The three batches of microcapsules were mixed, coated on a support, and dried to provide a full color imaging sheet.

| Internal Phase A (420 nm) | |
|---|---|
| TMPTA | 35 g |
| DPHPA | 15 g |
| 3-Thenoyl-7-diethylamino coumarin | 15 g |
| 2-Mercaptobenzoxazole (MBO) | 2.0 g |
| Pentamethylaniline (PMA) | 1.0 g |
| Reakt Yellow (BASF) | 5.0 g |
| SF-50 (Union Carbide Isocyanate) | 1.67 g |
| N-100 (Desmodur Polyisocyanate Resin) | 3.33 g |
| Internal Phase B (480 nm) | |
| TMPTA | 35 g |
| DPHPA | 15 g |
| 9-(4'-Isopropylcinnamoyl)-1,2,4-tetrahydro-3H, 6H, 10H[1]-benzopyrano[9, 9A,1-yl]quinolazine-10-one | 0.15 g |
| MBO | 1.0 g |
| PMA | 2.0 g |
| Magenta Color Former (HD-5100 Hilton Davis Chemical Co.) | 8.0 g |
| SF-50 | 1.67 g |
| N-100 | 3.33 g |
| Internal Phase C (570 nm) | |
| TMPTA | 50. g |
| Cationic Dye Compound No. 2 | 0.15 g |
| PMA | 2.00 g |
| Cyan Color Former (S-29663 Hilton Davis Chemical Co.) | 4.0 g |
| SF-50 | 1.67 g |
| N-100 | 3.33 g |

EXAMPLE 2

Capsule Preparation

1. Into a 600 ml stainless steel beaker, 110 g water and 4.6 g isobutylene maleic anhydride copolymer (dry) are weighed.
2. The beaker is clamped in place on a hot plate under an overhead mixer. A six-bladed, 45° pitch, turbine impeller is used on the mixer.
3. After thoroughly mixing, 4.0 g pectin (polygalacturonic acid methyl ester) is slowly sifted into the beaker. The mixture is stirred for 2 hours at room temperature (800–1200 rmp).

4. The pH is adjusted to 7.0 with 20% sulfuric acid.

5. The mixer is turned up to 3000 rpm and the internal phase is added over a period of 10-15 seconds. Emulsification is continued for 10 minutes. Magenta and yellow precursor phases are emulsified at 25-30° C. Cyan phase is emulsified at 45-50° C. (oil), 25-30° C. (water).

6. At the start of emulsification, the hot plate is turned up so heating continues during emulsification.

7. After 10 minutes, the pH is adjusted to 8.25 with 20% sodium carbonate, the mixing speed is reduced to 2000 rpm, and a solution of melamine-formaldehyde prepolymer is slowly added which is prepared by dispersing 3.9 g melamine in 44 g water, adding 6.5 g formaldehyde solution (37%) and heating at 60° C. until the solution clears plus 30 minutes.

8. The pH is adjusted to 6.0, the beaker is covered with foil and placed in a water bath to bring the temperature of the preparation to 65° C. When 65° C. is reached, the hot plate is adjusted to maintain this temperature for a two hour cure time during which the capsule walls are formed.

9. After curing, mixing speed is reduced to 600 rpm, formaldehyde scavenger solution (7.7 g urea and 7.0 g water) is added and the solution was cured another 40 minutes.

10. The pH is adjusted to 9.5 using a 20% NaOH solution and stirred overnight at room temperature.

Three batches of microcapsules were prepared as above for use in a full color imaging sheet using the three internal phase compositions set forth below.

| Yellow Forming Capsules (420 nm) | |
|---|---|
| TMPTA | 35 g |
| DPHPA | 15 g |
| 3-Thenoyl-7-diethylamino coumarin | 15 g |
| 2-Mercaptobenzoxazole (MBO) | 2.0 g |
| 2,6-Diisopropylaniline | 1.0 g |
| Reakt Yellow (BASF) | 5.0 g |
| N-100 (Desmodur Polyisocyanate Resin) | 3.33 g |
| Magenta Forming Capsules (550 nm) | |
| TMPTA | 50 g |
| Compound 8A | 0.2 g |
| 2,6-Diisopropylaniline | 2.0 g |
| HD5100 (Magenta color precursor from Hilton-Davis Chemical Co.) | 12.0 g |
| Cyan Forming Capsules (650 nm) | |
| TMPTA | 50 g |
| Compound 11 H | 0.31 g |
| 2,6-diisopropylaniline | 2.0 g |
| Cyan Precursor (CP-177 of Hilton-Davis Chemical Co.) | 6 g |

The three batches of microcapsules were blended together and coated on a support to provide an imaging material in accordance with the present invention.

The inventive compositions of the present invention may be used in connection with dental adhesives and compositions. Many commercially used adhesives are based upon photopolymerizable acrylate polymers. For example, commonly used adhesives are based upon bis-GMA (2,2-bis[4-(2-hydroxy-3-methacryloxypropoxy)phenyl]-propane, sometimes referred to as diglycidyl methacrylate of bisphenol A. Representatives of such compounds are set forth in U.S. Pat. Nos. 4,089,763; 4,459,193; 4,479,782; 4,490,115; 4,491,453; 4,515,930; 4,553,940; and at pages 501-508 and 515-517 of the Kirk-Othmer Encyclopedia of Chemical Technology, Third Edition, Volume 7 (1979). These compounds require a photoinitiator and may also include an amount of an inert dental filler material. Examples of dental filler materials include natural materials such as quartz, feldstone, pottery stone, wallastonite, mica, clay, kaolin, and marble; ceramics such as silica, aluminum, silicon nitride, boron carbide, boron nitride, soda glass, barium glass, strontium glass, borosilicate glass, and lanthanum-containing glass ceramic; and water-insoluble inorganic salts such as barium sulfate and calcium carbonate. The preferred photoinitiators were usually based upon alpha diketones. These initiators are disadvantageous as they are low in efficiency and absorptivity. Further, it is necessary to use either ultraviolet or blue light to initiate photopolymerization.

In accordance with the present invention, instead of using an alpha diketone initiator the inventive ionic dye-counter ion complexes are used as photoinitiators. Preferred photoinitiators are the cationic dye-borate anion complexes. Use of these initiators enables light emitted from a broad band visible light source to photoadhere dental work to teeth. Thus, the requirement of using harmful ultraviolet rays is obviated. Alternately, commercially available inexpensive lasers may be used as the light source for the photopolymerization reaction.

The dental compositions according to the present invention may also optionally include pigments, opacifiers, brightening agents, handling agents and other modificants.

The method of using the inventive dental adhesives and compositions follows, to an extent, the method currently practiced by those skilled in the art. The dental surface to be repaired is cleansed of decayed material and is acid etched to promote bonding. At this point, a bonding agent may be employed by coating it upon the surface to be repaired. The material of the present invention, including inert dental filler, is then applied to the dental surface and molded to the surface according to conventional practices. The dental surface, including adhesive, is then exposed to visible light from a light source and the presence of the ionic dye-counter ion complex generates free radicals which initiate free radical polymerization or crosslinking of the acrylate based adhesive material and subsequently cures the adhesive material. When used in this manner, the inventive composition functions both as an adhesive and as a dental restoration material.

Alternatively, the composition of the present invention may function solely as an adhesive. When used in this capacity, the dental surface is cleansed and the inventive adhesive is thereafter applied to the surface. Dental restoration material is then applied onto the adhesive material and the dental surface is exposed to visible light to adhere the restoration material to the dental surface. When used in this configuration, the restoration material should be transparent to enable light waves to pass through said restoration material and contact the adhesive to initiate photopolymerization.

Obtaining a desired color for the adhesive can be controlled by the time length of exposure to actinic radiation. Prolonged exposure to the light source will bleach the photoinitiator, thereby preventing unusual discoloration. Alternatively, if the retention of color is desired for cosmetic purposes, a lesser exposure time should be utilized.

The inventive photosensitive materials described herein also may be utilized in the field of photopolymer holography. A system known in the art contains a binder, photopolymerizable monomer, and photoinitiator coated onto a substrate as a film. The photoinitiator is selected to initiate polymerization of the monomer at a selected wavelength.

A typical representative photopolymer holographic system consists of a photopolymerizable monomer (40-50%), a cellulose acrylate butyrate binder (50-60%), and a bisimidazole initiator system (2-8%) sensitized to 488 nm. The photopolymerizable monomer is typically an acrylate. For example, the monomer may be triethyleneglycol diacrylate, triethylene glycol dimethacrylate, diethylene glycol diacrylate, decanediol diacrylate, or trimethylolpropane triacrylate.

In operation, the film made up of the above mentioned constituents is coated onto a substrate. Thereafter, the substrate is selectively illuminated with radiant light emitted from a laser in a predetermined pattern to create a desired image pattern. Images are created in the regions that have become depleted in monomer due to photopolymerization. Thereafter, the image is "fixed" by either removing the remaining monomer with an appropriate solution, or by a second, overall exposure to radiation.

In a typical embodiment, the initiator is selected to work in combination with a blue or ultraviolet light emitting laser source. The use of such a system is problematical in that the efficiency of the initiator is low, and the cost of the laser is high.

In the present invention, by utilizing a cationic dye-borate anion complex, the photoinitiator is capable of initiating photopolymerization when exposed to visible wavelengths. More specifically, when the initiator is designed to be sensitive to red or green light, the use of red or green lasers, respectively, to form the image may be utilized. This significantly decreases costs, as red and green light lasers are much more inexpensive than blue or ultraviolet light lasers.

In order to enhance the speed of the system, an autooxidant, such as N,N-dimethyl-2,6-diisopropylaniline may be included in the formulation. Further, optional thiols such as 2-mercaptobenzoxazole or 6-ethoxy-2-mercaptobenzothiazole, may also be utilized in the system.

It is further envisioned that additional discrimination and resolution may be obtained by using at least two different inventive photoinitiators which are sensitive to at least two different wavelengths of light emitted by lasers. In such a system, at least two lasers emitting light at wavelengths corresponding to the sensitivities of the initiators selected would be used.

An additional use of the inventive photoinitiators of the present invention is their ability to be combined with ultraviolet absorbers in photopolymerizable compounds to realize the twofold benefit of photopolymerization without corresponding ultraviolet degradation.

Many colored compounds are susceptible to degradation by ultraviolet radiation. What typically occurs is that the compounds, upon exposure to ultraviolet radiation, lose their true color and/or yellow. To combat the discoloring of the compounds, it is common for ultraviolet protectants to be added to the composition. The protectants typically take the form of an ultraviolet absorber.

Examples of protectants known and used in the art are: 2(3',5'-di-t-butyl-2'-hydroxy-phenyl)-5-chlorobenzotriazole, 2(3'-t-butyl-5'-methyl-2'-hydroxyphenyl)-5-chlorobenzotriazole, 2(2'-hydroxy-5'-met benzotriazole, 2-(2-hydroxy-5-t-octylphenyl)-benzotriazole, 2-hydroxy-4-n-octoxybenzophenone, 2,2'-dihydroxy-4-methoxybenzophenone, 2-hydroxy-4-methoxybenzophenone, 4-dodecyloxy-2-hydroxybenzo-phenone, and 2-ethoxyethyl p-methoxycinnamate.

Although the above-mentioned protectants succeed in their radiation protective function, when incorporated with photopolymerizable compositions containing ultraviolet absorbing photoinitiators, the protectants mask the function of the photoinitiators. As a result, photopolymerization cannot occur.

The inventors have discovered that the inventive cationic dye-borate anion compounds can be utilized in photopolymerizable compounds containing any of the above listed protectants. As the photoinitiators according to the present invention are sensitive to radiation in the visible spectrum, typically red light and green light, photopolymerization can proceed while in the presence of the ultraviolet protectants. Accordingly, compounds can be produced which are capable of photopolymerizing and are not susceptible to ultraviolet degradation. Such compounds may be used in house paints, automobile paints, autobodies and accessories, road signs, windows, plastic piping and polymeric parts used for supraatmospheric applications.

EXAMPLE 3

Four photosensitive compositions were formulated. Two of the compositions contained photoinitiators which were capable of generating free radicals upon exposure to ultraviolet radiation, one of the compositions contained a photoinitiator sensitive to green light, and one of the compositions contained a photoinitiator sensitive to red light. Each of the four compositions contained 2(-2'-hydroxy-5'-methylphenyl) benzotriazole, a commercial ultraviolet photoprotectant sold under the name of Tinuvin P by Ciba Geigy. The formulations were as follows:

| Formulation A | | |
|---|---|---|
| TMPTA | 50 | grams |
| Tinuvin P | 5 | grams |
| Irgacure 907 (UV initiator) | 12 | grams |
| Formulation B | | |
| TMPTA | 50 | grams |
| Tinuvin P | 5 | grams |
| Quanticure ITX (UV initiator) | 1 | gram |
| 2,6-diisopropyl-N,N-dimethylaniline (DIDMA) | 1 | gram |
| Formulation C ($\lambda max = 548$ nm) | | |
| TMPTA | 50 | grams |
| Tinuvin P | 5 | grams |
| DIDMA | 1 | gram |
| 1,1'-di-n-heptyl-3,3,3',3'-tetramethylindocarbocyaninetetraphenylbutylborate | 0.3 | grams |
| Formulation D ($\lambda max = 645$ nm) | | |
| TMPTA | 50 | grams |
| Tinuvin P | 5 | grams |
| DIDMA | 1 | gram |
| 1,1'-di-n-heptyl-3,3,3',3'-tetramethylindodicarbocyanine triphenyl-n-butylborate | 0.4 | grams |

One drop of each of the above formulations was placed between glass slides and exposed to radiation emitted from one General Electric F1518-CW fluorescent tube at a distance of 10 cm. The times for noticeable polymerization and total slide immobilization are shown in Table 3.

TABLE 3

| Formulation | Polymerization Time | Slide Immobilization Time |
|---|---|---|
| A | greater than 120 sec. | greater than 120 sec. |
| B | greater than 120 sec. | greater than 120 sec. |
| C | 10 sec. | 17 sec. |
| D | 15 sec. | 24 sec. |

EXAMPLE 4

Formulations A, B, C and D of Example 3 were coated onto separate 5 mil polyethylene terephthalate strips by using a #18 Meyer bar. Strips of each coating were placed in a glass-covered frame and the frame was flushed with argon for 10 minutes. The tubes were then exposed to radiation from two General Electric F1518-CW fluorescent tubes at a distance of 20 centimeters for 30 seconds. The cover of the frame was removed and the sample strips were inspected. Formulation A exhibited no apparent photopolymerization. Formulation B showed a slight amount of photopolymerization, but the strip was very tacky. Formulations C and D had cured to hard films, demonstrating that photopolymerization was complete.

A further use of the inventive photoinitiators is their ability to aid in the formulation of three dimensional models using computer controlled lasers. In current practice three dimensional models have been prepared by utilizing ultraviolet radiation generated from a computer controlled laser to contact a solution containing a photopolymerizable composition.

The operation of such a system begins with the use of a computer with attached monitor to produce a two-dimensional or synthetic three-dimensional image by using commonly available software programs. The computer is then interfaced separately to an ultraviolet laser and to a movable piston. The piston is located in a solution containing a photopolymerizable monomer and an ultraviolet sensitive photoinitiator, and the piston is capable of upward and downward movement within the solution, the movement of the piston being effectuated by the computer. Mounted onto the piston at its upper surface is a base which holds the model to be formed. The laser is in optical contact with the solution.

Once all of the components are connected the model is produced by the "tracing" of the two-dimensional monitor to transfer its image to the solution to form a three-dimensional model on a line by the line basis. By use of the computer, whether an image is to be transferred from a given line to the solution is determined by whether the laser is activated. If an image is to be produced for a given line, the laser is actuated by the computer to selectively expose the solution to ultraviolet radiation to initiate photopolymerization via the photoinitiator and to polymerize the exposed areas, causing these areas to harden. After tracing has been completed for a given line, the procedure is repeated for the next line and the piston raises or lowers the base appropriately to correspond to the shift in lines. This procedure is completed until all lines have been traced and the complete model has been produced. The model is then removed from the base.

Although the use of such a system provides an attractive alternative to manual model formulation, the system suffers in that it requires the use of ultraviolet lasers and ultraviolet sensitive photoinitiators. The use of ultraviolet lasers is undesirable because such lasers are expensive, typically have a short lifetime, and have optical systems which are not completely reliable.

The inventors have discovered that if visible light-sensitive photoinitiators capable of absorbing radiation in the visible spectrum and producing free radicals which initiate free radical polymerization or crosslinking, and monomers which are free radical addition photopolymerizable or crosslinkable are used in the model producing bath, the requirement of using ultraviolet lasers is obviated as photopolymerization can occur by exposure of the bath to visible light. Preferred photoinitiators are cationic dye-borate anion compounds sensitive to either red or green light. By using these initiators, the wavelength emitted by the laser used for polymerizing the solution would correspond to the sensitivity of the photoinitiator. The use of visible light lasers provides the two-fold benefit of lowering costs of the system and improving the quality of the model produced due to the superior and more reliable optical qualities of the laser used.

In an additional embodiment, if it is desired to create a model having multiple colors, the above procedure can be repeated using multiple baths corresponding to the numbers of colors desired. Each bath would contain a polymerizable monomer and a photoinitiator having a sensitivity corresponding to the color of light emitted by the laser acting upon the solution. Tracing would be repeated in each bath until the final object, having multiple colors, is produced.

It is envisioned that the model formulation system may be used to fabricate models for producing automobile parts, hardware, or any other mechanical parts capable of being generated by computer design.

The photosensitive compositions of the present invention are also useful in coating surfaces under water. There has long been a need for systems to control corrosion and biological fouling on underwater surfaces. The first underwater-applicable coatings were viscous epoxy-polyamide materials. These materials were applied by hand and cured slowly at temperatures below 60° F. (16° C.). Until cured, the coatings were susceptible to wave damage.

Methods for repairing concrete offshore structures underwater have also been desired. Techniques for the underwater placement of concrete have been available, however, the properties of the repaired structure do not compare favorably with the original structure which was cast above water. Polymer concretes such as polyethylene oxide have found use in this area. The repair must protect the steel reinforcement and prevent its corrosion and restore and preferably increase the strength of the structure.

A system for applying protective coatings to underwater surfaces and which permits damage or weathered coatings to be repaired on fixed or floating structures has long been sought. Radiation curable compositions are particularly desirable for such applications because they can be set rapidly and therefore are less susceptible to damage.

It has been found that the light sensitive compositions of the present invention can be fully cured under water. For use in underwater applications, the compositions are preferably prepared using water insoluble monomers. Particularly preferred monomers are acrylates and some urethanes, those which can be free radical polymerized. In addition, the compositions may be modified to include corrosion inhibitors, biocides and/or wetting agents such as fatty acids, waxes and oils to enhance the compositions ability to wet immersed surfaces and displace surface water.

In most applications it will be desirable to carry out some form of surface preparation such as abrasive blasting, water blasting, wire brushing, or the like to remove loose debris and any underwater growth as well as to roughen the surface and thereby improve adhesion.

One example of a formulation designed for underwater application contains 0.2 wt.% of a cyanine borate photoinitiator, 3.8 wt.% pentamethylaniline, 96.0 wt.% TMPTA. Though this mixture cures brittle, it does polymerize. A better composition would be one which includes a copolymer to better enhance the properties of the film.

Having described the invention in detail and by reference to preferred embodiments thereof, it will be apparent that modifications and variations are possible without departing from the scope of the invention defined in the appended claims.

What is claimed is:

1. A photohardenable composition comprising a free radical addition polymerizable or crosslinkable compound, an ionic dye-reactive counter ion compound and a thiol, said ionic dye-reactive counter ion compound being capable of absorbing actinic radiation and producing free radicals which initiate free radical polymerization or crosslinking of said polymerizable or crosslinkable compound and being a stable non-transient compound prior to exposure to said actinic radiation.

2. The photohardenable composition of claim 1 wherein said compound is an anionic dye compound.

3. The composition according to claim 2 wherein said thiol is selected from the group consisting of mercaptobenzoxazoles, mercaptotetrazines and mercaptotriazines.

4. The composition according to claim 3 wherein said thiol is selected from the group consisting of 2-mercaptobenzothiazole, 6-ethoxy-2-mercaptobenzothiazole, 2-mercaptobenzoxazole, 4-methyl-4H-1,2,4-triazole-3-thiol, 2-mercapto-1-methylimidazole, 2-mercapto-5-methylthio-1,3,4-thiadiazole, 5-n-butylthio-2-mercapto-1,3,4-thiadiazole, 4-methoxybenzenethiol, 1-phenyl-1H-tetrazole-5-thiol, 4-phenyl-4H-1,2,4-triazole-3-thiol, 2-mercaptobenzimidazole, pentaerythritol tetrakis(mercaptoacetate), pentaerythritol tetrakis(3-mercaptoproprionate), trimethylolpropane tris (mercapto-acetate), trimethylolpropane tris (3-mercaptopropionate), 4-acetamidothiophenol, mercaptosuccinic acid, dodecanethiol, 2-mercaptopyridine, 4-mercaptopyridine, 2-mercapto-3H-quinazoline, and 2-mercaptothiazoline.

5. The photohardenable composition of claim 1 wherein said ionic dye-reactive counter ion compound is a cationic dye-borate anion complex.

6. The photohardenable composition of claim 5 wherein said cationic dye-borate anion complex is represented by the formula (I):

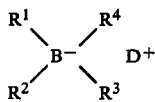

(I)

where D is a cationic dye moiety; and $R^1$, $R^2$, $R^3$ and $R^4$ are the same or different and selected from the group consisting of alkyl, aryl, aralkyl, alkaryl, alkenyl, alkynyl, alicyclic, heterocyclic, and allyl groups.

7. The photohardenable composition of claim 6 wherein at least one of $R^1$, $R^2$, $R^3$ and $R^4$ is an alkyl group.

8. The photohardenable composition of claim 7 wherein said cationic dye is selected from the group consisting of cationic cyanine, carbocyanine, hemicyanine, rhodamine, and azamethine dyes.

9. The composition according to claim 5 wherein said thiol is a thiol selected from the group consisting of mercaptobenzoxazoles, mercaptotetrazines and mercaptotriazines.

10. The composition according to claim 9 wherein said thiol is selected from the group consisting of 2-mercaptobenzothiazole, 6-ethoxy-2-mercaptobenzothiazole, 2-mercaptobenzoxazole, 4-methyl-4H-1,2,4-triazole-3-thiol, 2-mercapto-1-methylimidazole, 2-mercapto-5-methylthio-1,3,4-thiadiazole, 5-n-butylthio-2-mercapto-1,3,4-thiadiazole, 4-methoxybenzenethiol, 1-phenyl-1H-tetrazole-5-thiol, 4-phenyl-4H-1,2,4-triazole-3-thiol, 2-mercaptobenzimidazole, pentaerythritol tetrakis(mercaptoacetate), pentaerythritol tetrakis(3-mercaptoproprionate), trimethylolpropane tris (mercapto-acetate), trimethylolpropane tris (3-mercaptopropionate), 4-acetamidothiophenol, mercaptosuccinic acid, dodecanethiol, 2-mercaptopyridine, 4-mercaptopyridine, 2-mercapto-3H-quinazoline, and 2-mercaptothiazoline.

11. A photosensitive material comprising a support having a layer of a photohardenable composition on the surface thereof, said composition comprising a free radical addition polymerizable or crosslinkable compound, an ionic dye-reactive counter ion compound and a thiol, said ionic dye-reactive counter ion compound being capable of absorbing actinic radiation and producing free radicals which initiate free radical polymerization or crosslinking of said polymerizable or crosslinkable compound and being a stable non-transient compound prior to exposure to said actinic radiation.

12. The photosensitive material of claim 11 wherein said complex is an anionic dye complex.

13. The photosensitive material according to claim 12 wherein said thiol is a thiol selected from the group consisting of mercaptobenzoxazoles, mercaptotetrazines and mercaptotriazines.

14. The photosensitive material according to claim 13 wherein said thiol is selected from the group consisting of 2-mercaptobenzothiazole, 6-ethoxy-2-mercaptobenzothiazole, 2-mercaptobenzoxazole, 4-methyl-4H-1,2,4-triazole-3-thiol, 2-mercapto-1-methylimidazole, 2-mercapto-5-methylthio-1,3,4-thiadiazole, 5-n-butylthio-2-mercapto-1,3,4-thiadiazole, 4-methoxybenzenethiol, 1-phenyl-1H-tetrazole-5-thiol, 4-phenyl-4H-1,2,4-triazole-3-thiol, 2-mercaptobenzimidazole, pentaerythritol tetrakis(mercaptoacetate), pentaerythritol tetrakis(3-mercaptoproprionate), trimethylolpropane tris (mercapto-acetate), trimethylolpropane tris (3-mercaptopropionate), 4-acetamidothiophenol, mercaptosuccinic acid, dodecanethiol, 2-mercaptopyridine, 4-mercaptopyridine, 2-mercapto-3H-quinazoline, and 2-mercaptothiazoline.

15. The photosensitive material of claim 11 wherein said ionic dye-reactive counter ion compound is a cationic dye-borate anion complex.

16. The photosensitive material of claim 15 wherein said cationic dye-borate anion complex is represented by the formula (I)

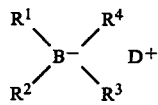

(I)

where D is a cationic dye moiety; and $R^1$, $R^2$, and $R^3$ and $R^4$ are the same or different and selected from the group consisting of alkyl, aryl, aralkyl, alkaryl, alkenyl, alkynyl, alicyclic, heterocyclic, and allyl groups.

17. The photosensitive material of claim 16 wherein at least one of $R^1$, $R^2$, $R^3$ and $R^4$ is an alkyl group and at least one is an aryl group.

18. The photosensitive material of claim 17 wherein said cationic dye is selected from the group consisting of cationic cyanine, carbocyanine, hemicyanine, rhodamine, and azamethine dyes.

19. The composition according to claim 15 wherein said thiol is a thiol selected from the group consisting of mercaptobenzoxazoles, mercaptotetrazines and mercaptotriazines.

20. The composition according to claim 19 wherein said thiol is selected from the group consisting of 2-mercaptobenzothiazole, 6-ethoxy-2-mercaptobenzothiazole, 2-mercaptobenzoxazole, 4-methyl-4H-1,2,4-triazole-3-thiol, 2-mercapto-1-methylimidazole, 2-mercapto-5-methylthio-1,3,4-thiadiazole, 5-n-butylthio-2-mercapto-1,3,4-thiadiazole, 4-methoxybenzenethiol, 1-phenyl-1H-tetrazole-5-thiol, 4-phenyl-4H-1,2,4-triazole-3-thiol, 2-mercaptobenzimidazole, pentaerythritol tetrakis(mercaptoacetate), pentaerythritol tetrakis(3-mercaptoprionate), trimethylolpropane tris (mercapto-acetate), trimethylolpropane tris (3-mercaptopropionate), 4-acetamidothiophenol, mercaptosuccinic acid, dodecanethiol, 2-mercaptopyridine, 4-mercaptopyridine, 2-mercapto-3H-quinazoline, and 2-mercaptothiazoline.

21. The photosensitive material of claim 12 wherein said photohardenable composition is microencapsulated.

22. The photosensitive material of claim 15 wherein said photohardenable composition is microencapsulated.

23. The photosensitive material of claim 21 wherein said material is useful in forming full color images and said microcapsules include a first set of microcapsules having a cyan image-forming agent associated therewith, a second set of microcapsules having a magenta image-forming agent associated therewith and a third set of microcapsules having a yellow image-forming agent associated therewith, at least one of said first, second and third sets of microcapsules containing said photohardenable composition contain said ionic dye-counter ion compound.

24. The photosensitive material of claim 22 wherein said material is useful in forming full color images and said microcapsules include a first set of microcapsules having a cyan image-forming agent associated therewith, a second set of microcapsules having a magenta image-forming agent associated therewith and a third set of microcapsules having a yellow image-forming agent associated therewith, at least one of said first, second and third sets of microcapsules containing said photohardenable composition contain said ionic dye-counter ion compound.

* * * * *